US007107088B2

(12) United States Patent
Aceti

(10) Patent No.: US 7,107,088 B2
(45) Date of Patent: Sep. 12, 2006

(54) PULSE OXIMETRY METHODS AND APPARATUS FOR USE WITHIN AN AUDITORY CANAL

(75) Inventor: John Gregory Aceti, West Windsor, NJ (US)

(73) Assignee: Sarnoff Corporation, Princeton, NJ (US)

( * ) Notice: Subject to any disclaimer, the term of this patent is extended or adjusted under 35 U.S.C. 154(b) by 190 days.

(21) Appl. No.: 10/847,678

(22) Filed: May 17, 2004

(65) Prior Publication Data

US 2005/0049471 A1 Mar. 3, 2005

Related U.S. Application Data

(60) Provisional application No. 60/497,890, filed on Aug. 25, 2003.

(51) Int. Cl.
*A61B 5/00* (2006.01)
*A61B 5/02* (2006.01)

(52) U.S. Cl. ........................................ 600/340; 600/502

(58) Field of Classification Search ................ 600/310, 600/322, 323, 340, 344, 500, 502, 549
See application file for complete search history.

(56) References Cited

U.S. PATENT DOCUMENTS

| 2,414,747 | A | 1/1947 | Kirschbaum |
| 3,858,574 | A | 1/1975 | Page |
| 3,910,257 | A | 10/1975 | Fletcher et al. |
| 4,312,358 | A | 1/1982 | Barney |
| 4,621,643 | A | 11/1986 | New, Jr. et al. |
| 4,662,360 | A | 5/1987 | O'Hara et al. |
| 4,754,748 | A | 7/1988 | Antowski |
| 4,790,324 | A | 12/1988 | O'Hara et al. |
| 4,797,840 | A | 1/1989 | Fraden |
| 4,821,982 | A | 4/1989 | Van Patten |
| 4,934,372 | A | 6/1990 | Corenman et al. |
| 5,036,853 | A | 8/1991 | Jeffcoat et al. |
| 5,044,373 | A | 9/1991 | Northeved et al. |
| 5,058,586 | A | 10/1991 | Heinze |
| 5,109,849 | A | 5/1992 | Goodman et al. |
| 5,115,133 | A | 5/1992 | Knudson |
| 5,137,023 | A | 8/1992 | Mendelson et al. |
| 5,146,091 | A | 9/1992 | Knudson |
| 5,152,296 | A | 10/1992 | Simons |
| 5,167,235 | A | 12/1992 | Seacord et al. |
| 5,213,099 | A | 5/1993 | Tripp, Jr. |
| 5,297,554 | A | 3/1994 | Glynn et al. |
| 5,361,758 | A | 11/1994 | Hall et al. |

(Continued)

FOREIGN PATENT DOCUMENTS

GB 2 210 168 A 1/1989

(Continued)

*Primary Examiner*—Eric F. Winakur
(74) *Attorney, Agent, or Firm*—Lowenstein Sandler, PC

(57) ABSTRACT

Methods and apparatus for detecting oxygen saturation levels in blood from within an auditory canal of a living being proximal to a tympanic membrane are disclosed. The auditory canal is lined with tissue and includes a proximal bend and a distal bend located between the proximal bend and the tympanic membrane. Oxygen levels are detected by emitting one or more wavelengths of light into a first position on the tissue of the auditory canal in a first region defined by the distal bend and the tympanic membrane. The wavelengths of light are then sensed at a second position on the tissue of the auditory canal in the first region. A blood oxygen saturation level and/or pulse rate is then calculated responsive to intensity information corresponding to the wavelengths of light detected at the second position.

18 Claims, 6 Drawing Sheets

U.S. PATENT DOCUMENTS

| | | |
|---|---|---|
| 5,469,855 A | 11/1995 | Pompei et al. |
| 5,626,139 A | 5/1997 | Szeles et al. |
| 5,673,692 A | 10/1997 | Schulze et al. |
| 5,812,992 A | 9/1998 | de Vries |
| 5,895,371 A | 4/1999 | Levitas et al. |
| 6,004,274 A | 12/1999 | Nolan et al. |
| 6,047,205 A | 4/2000 | Pompei |
| 6,053,887 A | 4/2000 | Levitas et al. |
| 6,075,443 A | 6/2000 | Schepps et al. |
| 6,078,829 A | 6/2000 | Uchida et al. |
| 6,080,110 A | 6/2000 | Thorgersen |
| 6,115,621 A | 9/2000 | Chin |
| 6,205,227 B1 | 3/2001 | Mahoney et al. |
| 6,231,560 B1 | 5/2001 | Bui et al. |
| 6,253,871 B1 | 7/2001 | Aceti |
| 6,254,526 B1 | 7/2001 | Juneau et al. |
| 6,283,915 B1 | 9/2001 | Aceti et al. |
| 6,289,309 B1 | 9/2001 | deVries |
| 6,343,223 B1 | 1/2002 | Chin et al. |
| 6,358,216 B1 | 3/2002 | Kraus et al. |
| 6,398,727 B1 | 6/2002 | Bui et al. |
| 6,410,997 B1 | 6/2002 | Sjursen et al. |
| 6,473,511 B1 | 10/2002 | Aceti et al. |
| 6,556,852 B1 | 4/2003 | Achulze et al. |
| 6,579,242 B1 | 6/2003 | Bui et al. |
| 6,691,087 B1 | 2/2004 | Parra et al. |
| 2001/0033664 A1 | 10/2001 | Poux et al. |
| 2002/0006209 A1 | 1/2002 | Mahoney et al. |
| 2002/0015506 A1 | 2/2002 | Aceti et al. |
| 2002/0027996 A1 | 3/2002 | Leedom et al. |
| 2003/0092975 A1 | 5/2003 | Casscells, III et al. |

FOREIGN PATENT DOCUMENTS

| | | |
|---|---|---|
| GB | 2 302 945 A | 5/1997 |
| WO | WO 97/09927 | 3/1997 |
| WO | WO 01/17109 A1 | 3/2001 |

PULSE OXIMETRY METHODS AND APPARATUS FOR USE WITHIN AN AUDITORY CANAL

CROSS REFERENCE TO RELATED APPLICATION

This application claims the benefit of U.S. Provisional Application No. 60/497,890, filed Aug. 25, 2003, the contents of which are incorporated herein by reference.

FIELD OF THE INVENTION

The present invention relates to the field of medical devices and, more particularly, to noninvasive pulse oximetry methods and apparatus for use inside an auditory canal of a living being.

BACKGROUND OF THE INVENTION

An oximeter calculates blood oxygen saturation levels within a living being from the different rates at which oxygenated hemoglobin (oxyhemoglobin) and reduced hemoglobin (deoxyhemoglobin) within vascular tissue of the living being absorb light of different wavelengths. Typically, two wavelengths of light are used where one wavelength is much less sensitive to blood oxygen saturation levels than the other. The wavelength of light that is less sensitive to oxygen saturation levels serves as a constant against which the wavelength of light that is more sensitive to oxygen saturation levels is compared in order to calculate blood oxygen saturation levels.

The measurement of oxygen saturation levels ("oximetry") is a critical physiologic measurement for critical care patients. Presently, sensors for use with oximeters to measure oxygen saturation levels in vascular tissue are designed for placement on a finger, ear lobe, foot, or in an outer portion of the auditory canal. These sensors are subject to motion artifacts that may result in inaccurate measurements. Accordingly, improved oximetry methods and apparatus are needed that are not subject to this limitation. The present invention addresses this need among others.

SUMMARY OF THE INVENTION

The present invention is embodied in methods and apparatus for detecting oxygen saturation levels in blood from within an auditory canal of a living being proximal to a tympanic membrane. The auditory canal is lined with tissue and includes a proximal bend and a distal bend located between the proximal bend and the tympanic membrane. Oxygen levels are measured by emitting one or more wavelengths of light into a first position on the tissue of the auditory canal in a first region defined by the distal bend and the tympanic membrane; sensing the wavelengths of light at a second position on the tissue of the auditory canal in the first region, the second position being spaced from the first position; and calculating at least one of (i) a blood oxygen saturation level and (ii) a pulse rate responsive to intensity information corresponding to the wavelengths of light detected at the second position.

BRIEF DESCRIPTION OF THE DRAWINGS

The invention is best understood from the following detailed description when read in connection with the accompanying drawings, with like elements having the same reference numerals. This emphasizes that, according to common practice, the various features of the drawings are not drawn to scale. On the contrary, the dimensions of the various features are arbitrarily expanded or reduced for clarity. When a plurality of similar elements are present, a single reference numeral may be assigned to the plurality of similar elements with a small letter designation referring to specific elements. When referring to the elements collectively or to a non-specific one or more of the elements, the small letter designation may be dropped. Included in the drawings are the following figures.

DETAILED DESCRIPTION OF THE INVENTION

Figure 1:
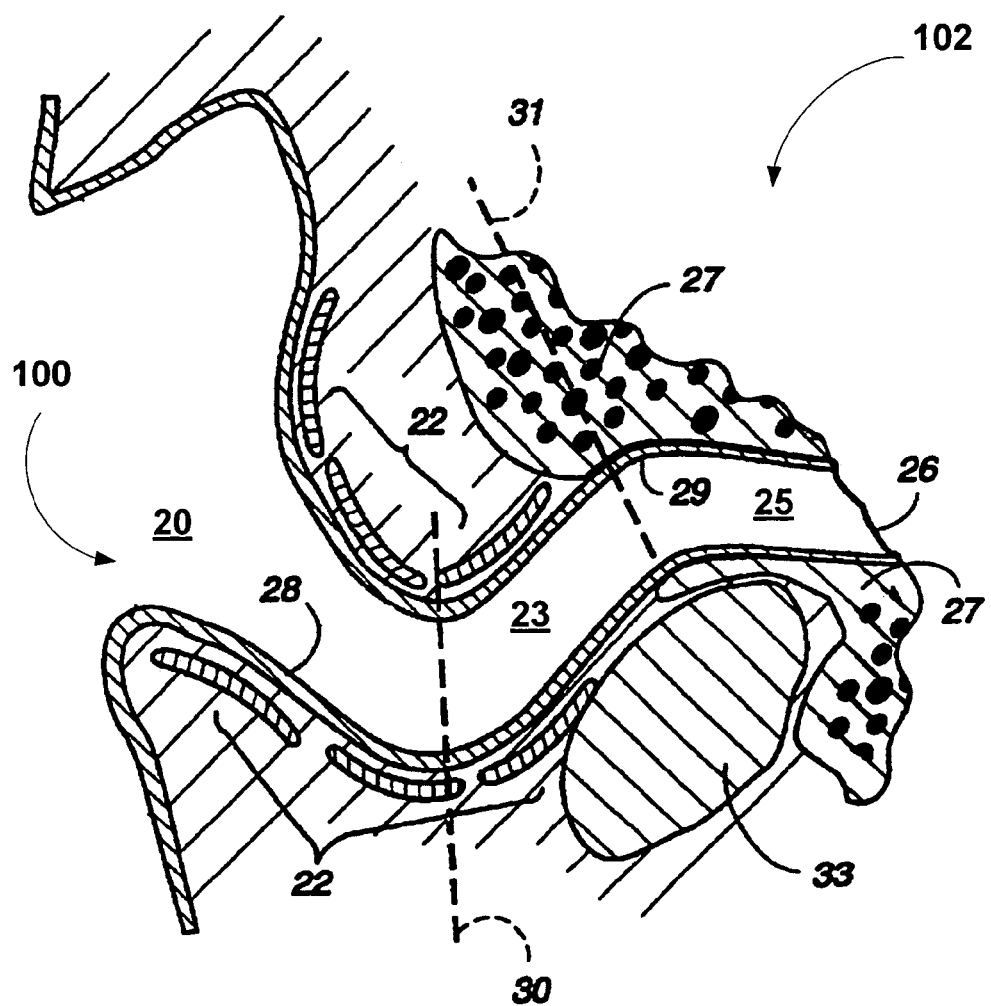
FIG. 1 is a cross sectional anatomical illustration of an auditory canal and surrounding structure.

FIG. 1 show a cross-sectional anatomical view of an auditory canal 100 in the transverse plane of a portion 102 of a head. The auditory canal 100 is generally S-shaped and can be described as having three regions. A first region 20 is the medial concha cavity, which is surrounded by cartilaginous tissue 22. A second region 23, which is separated from the first region 20 by a first bend 30 (the "proximal bend"), is also surrounded by cartilaginous tissue 22. A third region 25, which is separated from the second region 23 by a second bend 31 (the "distal bend"), defines the final auditory canal region near the tympanic membrane 26 and is surrounded by dense bony tissue 27.

Vascular tissue 28 covering the first and second regions 20 and 23 is relatively thick and has a well developed subcutaneous layer that allows some expansion to occur. In contrast, vascular tissue 29 covering the third region 25 is relatively thin and, thus, little or no tolerance for expansion exists in this region.

Mandibular motion associated with activities such as talking, chewing, yawning, and biting deforms the first and second regions 20 and 23 of the auditory canal 100. This deformation is generally caused by the asymmetric stresses from the actions of the mandibular condyle 33 on neighboring cartilaginous tissue 22. These deformations have radial components, e.g. constrictions, and axial components, i.e. inward and outward motion, which may result in motion artifacts in known oximetry sensors positioned within the first or second regions 20 and 23. The third region 25, which is surrounded by bony tissue 27, is less susceptible to deformation due to mandibular motion. Additional details regarding the auditory canal may be found in U.S. Pat. No. 5,701,348, which is incorporated fully herein by reference.

Figure 2:
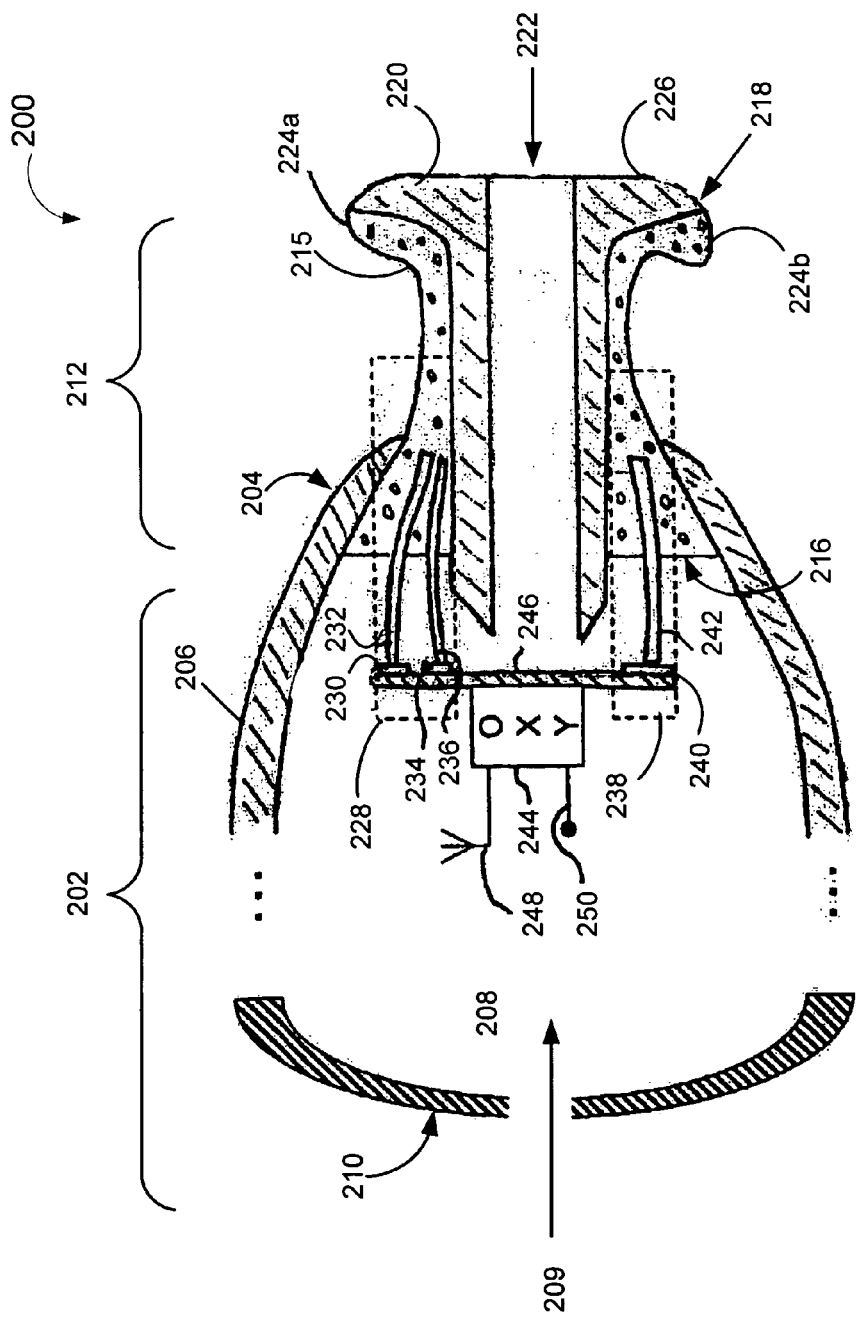
FIG. 2 is a cross-sectional view of an exemplary oximetry sensor in accordance with the present invention.

FIG. 2 depicts an exemplary oximetry sensor 200 and will be described with reference to the auditory canal 100 of FIG. 1. The oximetry sensor 200 is configured to measure oxygen saturation levels in the vascular tissue 29 within the third region 25 of the auditory canal 100. A first portion 202 of the oximetry sensor 200 is configured for placement in the second region 23 of the auditory canal 100, i.e., between the first bend 30 and the second bend 31. The first portion 202 includes a distal end 204 that extends toward the tympanic membrane 26 when the oximetry sensor 200 is positioned within the auditory canal 100. In an exemplary embodiment, the first portion 202 includes an outer surface (shell) 206 that is relatively rigid and shaped to conform to the contours of the second region 23.

In an exemplary embodiment, the outer surface 206 of the first portion 202 is substantially smooth and the first portion 202 further includes a hollow body portion 208 that extends from the distal end 204 to an outer end 210 that is substantially opposite the distal end 204. The hollow body portion 208 defines an elongated passage 209 that extends between the outer end 210 and the distal end 204 of the first portion 202 for communication of acoustic signals through the first portion 202. The hollow body portion 208 may be configured such that light is not passed by the hollow passage to the vascular tissue 29 in the third region 25.

Figure 3:
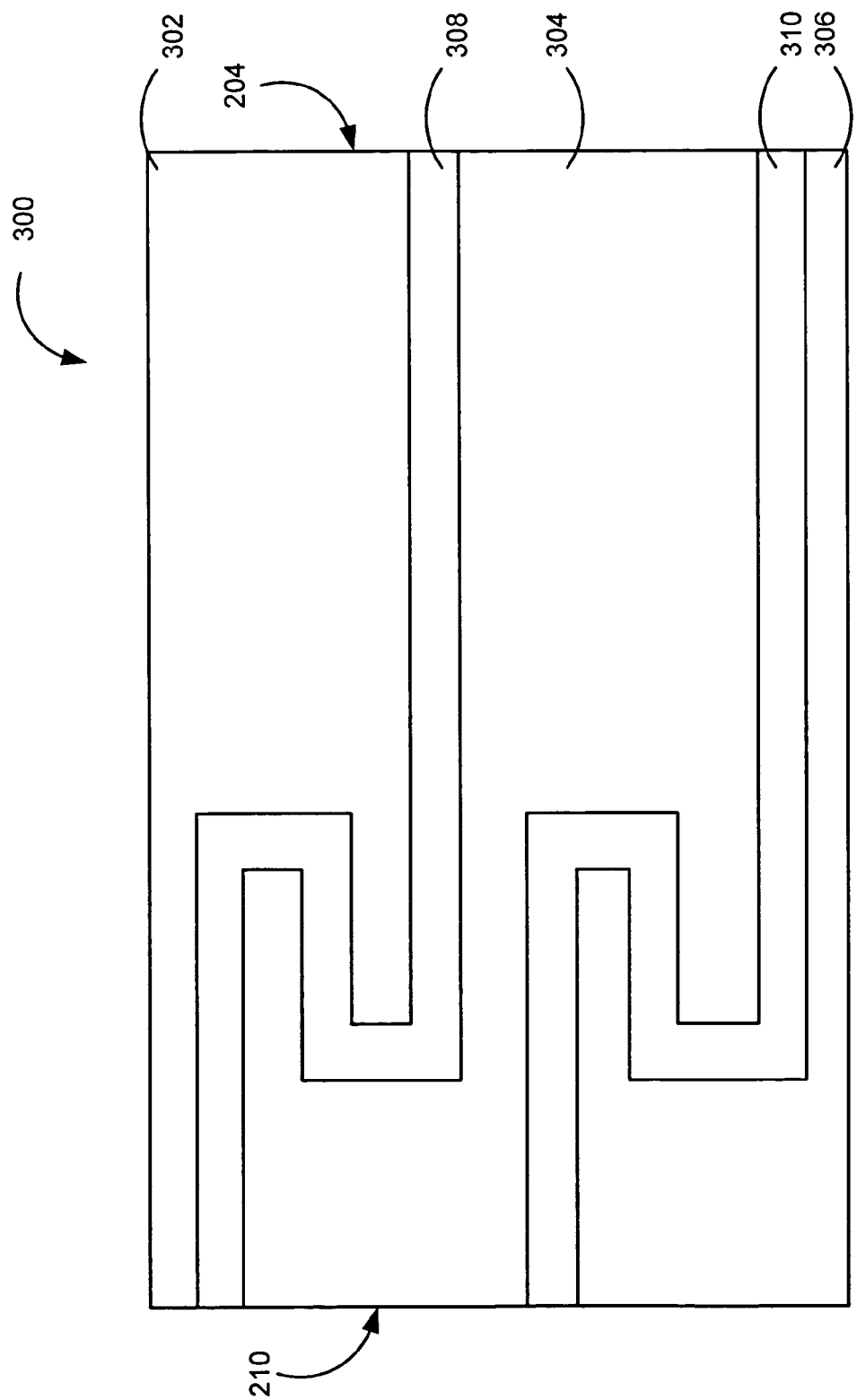
FIG. 3 is a surface view of a portion of an exemplary outer surface of the oximetry sensor of FIG. 2.

In an alternative exemplary embodiment, the outer surface 206 of the first portion 202 includes one or more protrusions (fins, bumps, etc.) that form channels extending from the outer end 210 to the distal end 204 of the first portion 202 in addition to, or instead of, the hollow body portion 208. FIG. 3 represents an exemplary portion 300 of the outer surface 206 (FIG. 2) between the outer end 210 and the distal end 204. The exemplary portion 300 includes protrusions (represented by a first protrusion 302, a second protrusion 304, and a third protrusion 306). The illustrated first and second protrusions 302 and 304 define a first channel 308 and the second and third protrusions 304 and 306 define a second channel 310. The channels 308 and 310 each have a "maze-like" configuration that doubles back on itself between the outer end 210 and the distal end 204 to allow acoustic signals to pass through the second region 23 (FIG. 1) to a second portion 212 (FIG. 2) while blocking light from reaching the vascular tissue 29 in the third region 25.

In an exemplary embodiment, the protrusions are sized to comfortably support the first portion 202 within the auditory canal 100 while allowing air (sound) to flow freely past the first portion 202. The protrusions act to centrally hold the first portion 202 in the second region 23 of the auditory canal 100 and comfortably touch the vascular tissue 28 of the auditory canal 100. Each protrusion may have a flat surface where it contacts the vascular tissue 28 to minimize discomfort. Although three protrusions are illustrated, fewer or more protrusions may be formed on the outer surface 206. Positioning a device within the auditory canal 100 negatively affect hearing, however, a hole larger than 2 mm, or an effective passage(s) having an area equivalent to a 2 mm hole or larger will substantially pass most low to high audio frequencies.

Referring back to FIG. 2, a second portion 212 of the oximetry sensor 200 is configured for placement in the third region 25 of the auditory canal 100, i.e., between the second bend 31 and the tympanic membrane 26. The second portion 212 includes optically transparent portions 224 and optically blocking portions 226 for use in measuring oximetry levels within the vascular tissue 29 of the third region 25, which is described in further detail below. The optically transparent portions 224 form channels and/or islands within the optically blocking portions 226. An outer surface 214 of the second portion 212 is configured to abut at least a portion of the vascular tissue 29 lining the auditory canal 100 in the third region 25. Due to the dense bony tissue 27 surrounding the third region 25, positioning the second portion 212 within the third region 25 effectively isolates the second portion 212 from being directly affected by mandibular motion, thereby reducing oximetry false alarms associated with motion artifacts. Additionally, positioning the second portion 212 past the second bend 31 tends to "lock" the oximetry sensor 200 in position.

In an exemplary embodiment, the second portion 212 is movably coupled to the first portion 202. The second portion 212 includes a proximal end 216 and a tympanic end 218 that extends toward the tympanic membrane 26 when the oximetry sensor 200 is positioned within the auditory canal 100. Although positioning the second portion 212 within the third region 25 effectively isolates the second portion from being directly affected by mandibular motion, the second portion 212 may be indirectly affected by mandibular motion transferred to the second portion 212 through the first portion 202. Movably coupling the second portion 212 to the first portion 202 reduces the effect of this indirect mandibular motion on the second portion 212, thereby further reducing oximetry measurement false alarms due to motion artifacts.

In an exemplary embodiment, the second portion 212 further includes a hollow body portion 220 that defines an elongated passage 222 extending between the proximal end 216 and the tympanic end 218 of the second portion 212. The hollow body portion 220 is configured to communicate acoustic signals through the second portion 212 between the first portion 202 and the tympanic membrane 26. If each of the first and second portions 202 and 212 include elongated passages (e.g., elongated passages 209 and 222), acoustic signals originating from outside the auditory canal 100 may pass to the tympanic membrane 26.

In an exemplary embodiment, the second portion 212 is made of a flexible elastomer, which renders the second portion 212 movable with respect to the first portion 202. The flexible elastomer facilitates the navigation of the typical, nominally S-shaped centerline path of the auditory canal 100. The second portion 212 may be constructed of a low modulus, low durometer material to provide a high level of comfort for the user even when it is inserted into the third region 25 of the auditory canal 100. In addition, the hollow body portion 220 may be substantially tubular in shape and elongated to permit a continuum of deformations along its length so that its axis can conform to the axis of the auditory canal in the third region 25.

Figure 2A:
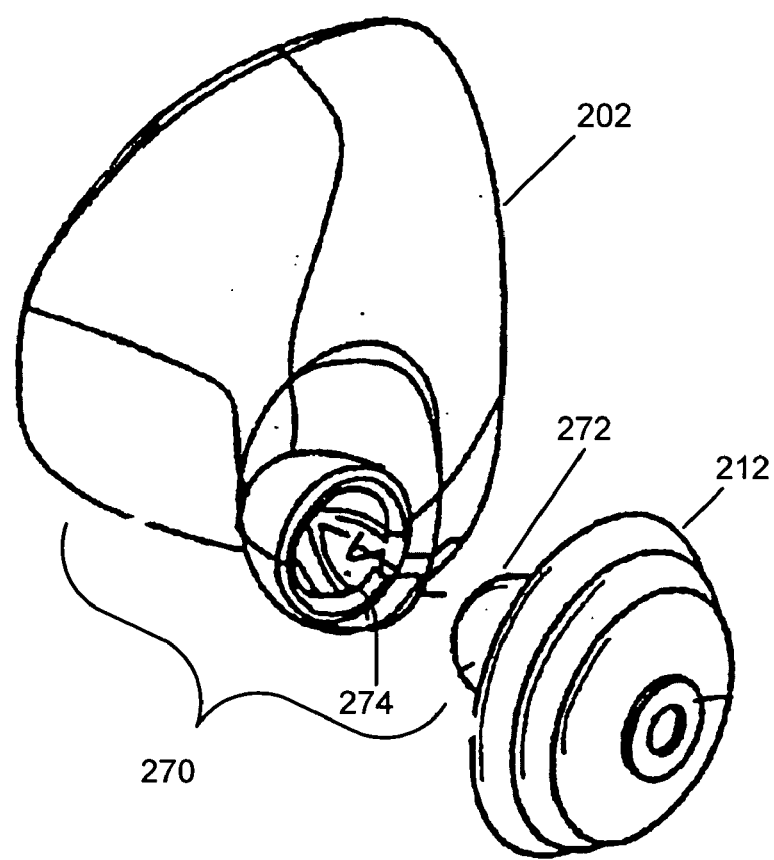
FIG. 2A is a perspective view of an alternative exemplary oximetry sensor in accordance with the present invention.

In an alternative exemplary embodiment, as depicted in FIG. 2A, a mechanical joint 270 may be positioned between the first portion 202 and the second portion 212 to render the second portion 212 movable relative to the first portion 202. The illustrated mechanical joint 270 includes a ball portion 272 and a ball receiving portion 274 configured to movably engage the ball portion 272. Examples of suitable mechanical joints may be found in U.S. Pat. No. 6,205,227 to Mahoney et al. titled PERITYMPANIC HEARING INSTRUMENT, which is commonly assigned with the present application and incorporated fully herein by reference.

Referring back to FIG. 2, an emitter 228 is positioned within the oximetry sensor 200 to emit light of two or more wavelengths from a first optically transparent portion 224a of the second portion 212 into a corresponding first position of the vascular tissue 29 when the oximetry sensor 200 is positioned within the auditory canal 100. The illustrated emitter 228 includes a first light source 230, a first light channel 232, a second light source 234, and a second light channel 236. In an exemplary embodiment, the first and second light sources 230 and 234 are positioned within the first portion 202 and the first and second light channels 232 and 234 are configured to direct light from the first and second light sources, respectively, to the first optically transparent portion 224a. In an alternative embodiment, the light sources 230 and 234 may be positioned within the second portion 212 with leads (not shown) for powering the light sources extending from a power source (not shown) in the first portion 202 to the first and second light sources in the second portion 212. The first and second light sources 230 and 234 may be light emitting diodes (LEDs, e.g., a 660 nm LED and an 805 nm LED) and the first and second light channels 232 and 236 may be optical fibers.

A detector 238 is positioned within the oximetry sensor 200 to detect light of the two or more wavelengths out of a second position of the vascular tissue 29 impinging a corresponding second optically transparent portion 224b of the second portion 212 when the oximetry sensor 200 is positioned within the auditory canal 100. The illustrated detector 238 includes a photodetector 240 (e.g., a photo diode) and a third light channel 242 (e.g., an optical fiber). In an exemplary embodiment, the photodetector 240 is positioned within the first portion 202 and the third light channel 242 is configured to direct light impinging the second optically transparent portion 224b of the second portion 212 through the second portion 212 to the photodetector 240 in the first portion 202. In an alternative exemplary embodiment, the photodetector 240 may be positioned within the second portion 212 with a lead (not shown) extending from the photodetector 240 to oximetry circuitry 244 in the first portion 202. The first and second optically transparent portions 224a and 224b may form channels on the surface of the second portion 212 for respectively emitting and detecting light along the channels to maximize coupling and to limit the effects of blockage do to wax build-up.

Figure 4A:
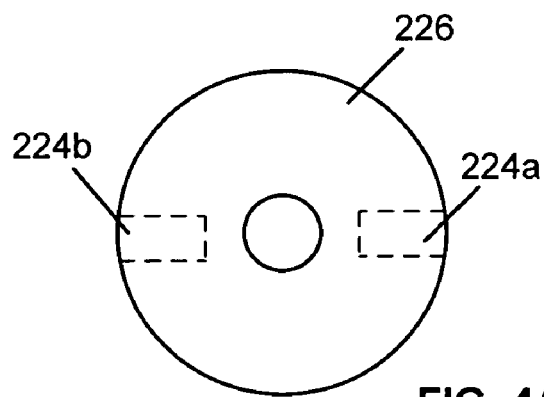
FIGS. 4A, 4B, and 4C are cross-sectional views of exemplary portions of the oximetry sensor.
Figure 4B:
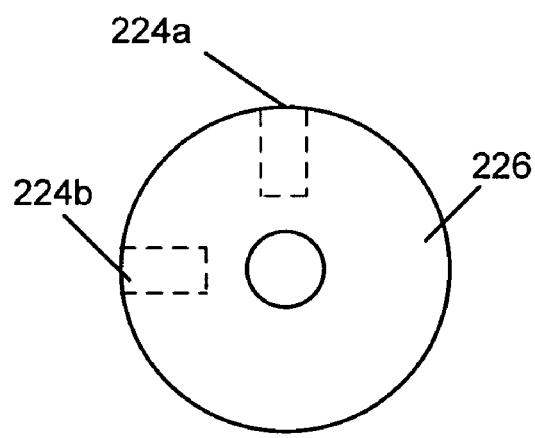
Figure 4C:
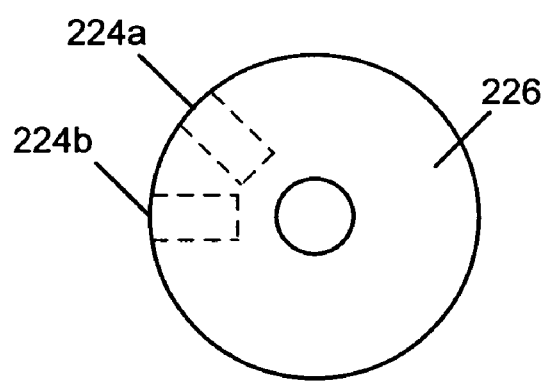

FIGS. 4A, 4B, and 4C depict cross sectional views of exemplary second portions 212 for delivering light to the first and second positions of the vascular tissue in the third region 25. The cross sectional views each include an optically blocking portion 226 and optically transparent portions 224. The illustrated cross sectional second portions each include two transparent portions 224—a light emitting optically transparent portion 224a and a light receiving optically transparent portion 224b. The light emitting portion 224a is coupled to the first and second light sources 230 and 234 (FIG. 2) and the light receiving portion 224b is coupled to the photodetector 240, e.g., via optical fibers 232, 236, and 242. The light emitting portion 224a emits light from the light sources to the first position of the vascular tissue 29 when the oximetry sensor 200 is positioned within the auditory canal and the light receiving portion 224b collects light from the second position of the vascular tissue 29 when the oximetry sensor 200 is positioned within the auditory canal.

In FIG. 4A, the light emitting portion 224a and the light receiving portion 224b are radially positioned substantially opposite one another, e.g., about 180 degrees apart, such that the first and second positions on the vascular tissue are on opposite sides of the second portion 212 (FIG. 2). In FIG. 4B, the light emitting portion 224a and the light receiving portion 224b are radially positioned approximately 90 degrees with respect to one another. In FIG. 4C, the light emitting portion 224a and the light receiving portion 224b are radially positioned approximately 45 degrees with respect to one another. In an exemplary embodiment, the light emitting portion 224a and the light receiving portion 224b are radially positioned relative to one another between about 5 degrees and 180 degrees. In an alternative exemplary embodiment, the light emitting portion and the light receiving portion may radially overlap, but be separated in a longitudinal direction by the optically blocking portion 226, e.g., along the length of the elongated passage 222 (FIG. 2) extending through the second portion 212.

Referring back to FIG. 2, the oximetry circuitry 244 is configured to process information corresponding to the two or more wavelengths of light received by the detector 238. In addition, the oximetry circuitry 244 may be configured to control the emitter 228. The oximetry circuitry 244 may be coupled to the emitter 228 and the detector 238 via traces of a circuit board 246. The oximetry circuitry 224 may be configured to calculate an oximetry value based on the received two or more wavelengths of light. In addition, the oximitry circuitry 244 may be configured to calculate pulse rate. Suitable methods for calculating oximetry levels and pulse rates will be understood by those of skill in the art.

The exemplary oximetry circuitry 244 further includes an emitter 248 for wireless transmission of information related to the two or more wavelengths of light and/or a port 250 for wired transmission of information related to the two or more wavelength of light. The information related to the two or more wavelengths of light may be values calculated by the oximetry circuitry 244 or raw data detected by the detector 238. A suitable oximetry circuit for use in the present invention will be understood by those of skill in the art.

Figure 5:
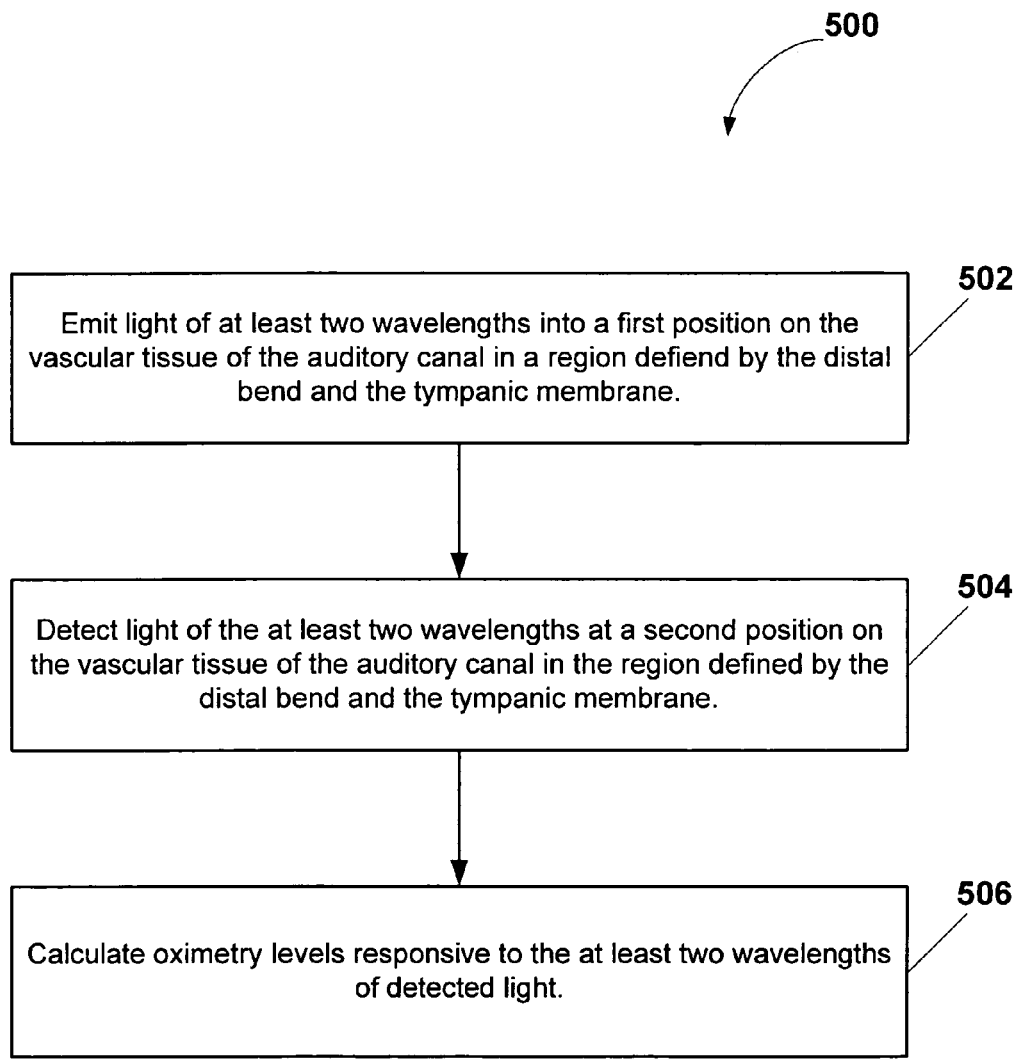
FIG. 5 is a flow chart of exemplary steps for determining oximetry levels in accordance with the present invention.

FIG. 5 depicts a flow chart 500 of exemplary steps for detecting oxygen saturation levels in blood from within an auditory canal of a living being. The steps are described with reference to FIGS. 1 and 2.

At block 502, the emitter 228 emits light of two or more wavelengths into a first position on the vascular tissue 29 of the auditory canal 100 in the third region 25, which is defined by the distal bend 31 and the tympanic membrane 26. At least one of the wavelengths of light is much less sensitive to blood oxygen saturation levels than at least one of the other wavelengths of light. The wavelength of light that is sensitive to blood oxygen saturation levels may be the isobestic wavelength, which for oxygenated blood is 805 nm, e.g., infrared light. After the oximetry sensor 200 is positioned within the auditory canal 100, the emitter 204 emits the two or more wavelengths of light, e.g., from light sources 230 and 234, responsive to the oximetry circuitry 244.

In an exemplary embodiment, the oximetry circuitry 244 is configured to modulate the emitter 228 to cause a first light source, e.g., light source 230, to emit light for one-third (⅓) of a proposed cycle time; to cause a second light source, e.g., light source 234, to emit light during a second one-third of the cycle time; and to cause no light to be emitted during a final one-third of the cycle time. During the period of time in which no light is emitted, the detector 238 may measure background light intensity levels for subtraction from the measure light intensity signals when light is being emitted to increase accuracy.

In an exemplary embodiment, the wavelengths of light are generated in the first portion 202 and are passed to the emitting optically transparent portion 224a of the second portion 212, e.g., via optical fibers 232 and 234, where they are emitted into the first position on the vascular tissue 29. In an alternative exemplary embodiment, the wavelengths of light originate in the second portion 212 responsive to electrical signal from the oximetry circuitry 244.

At block 504, the detector 238 detects the intensity of the two or more frequencies of light at a second position on the vascular tissue 29 of the auditory canal 100 in the third region 25. The second position is spaced from the first position and the light detected by the detector 228 is light that has passed through the vascular tissue 29 from the first position to the second position. In an exemplary embodiment, the detector 238 sequentially detects the light as emitted by the emitter 228.

In an exemplary embodiment, light from the second position of the vascular tissue 29 impinges upon the optically transparent portion 224b of the second portion 212 and is passed to the photo detector 240 in the first portion 202, e.g., via an optical fiber 242, for detection and communication to the oximetry circuitry 244. In an alternative exemplary embodiment, the light is detected in the second portion and an electrical signal including intensity information corresponding to the detected light is passed to the first portion, e.g., via a transmission line.

As used herein, the phrase "intensity information corresponding to the two or more frequencies of light" detected in the third region 25 may be used to refer to the actual light or to an electrical signal representing the actual light. In an exemplary embodiment, this information passes from the third region 25 to another region (e.g., within the auditory canal or outside of the auditory canal) distinct from the third region 25 through a flexible coupling (e.g., a flexible second portion 202 coupled to the first portion 212 or a mechanical joint connecting the first and second portions 202 and 212).

At block 506, the oximetry circuitry 244 calculates a blood oxygen saturation level responsive to the intensity information corresponding to the two or more wavelengths of light detected at the second position. Since one of the frequencies of light is less sensitive to oxygen saturation levels than the other, this frequency of light provides a "base-line" against which a frequency of light that is more sensitive to oxygen saturation can be compared in order to calculate blood oxygen saturation levels in a manner that will be understood by those of skill in the art. The oximetry circuitry 244 may alternatively or additionally calculate pulse rate responsive to the information in a manner that will also be understood by those of skill in the art. The absolute strength of the signal is dynamic and cyclic being responsive to the pulsitile arterial blood flow—peak to peak measurements determine pulse. For a modulated light source, the light source should be modulated at a frequency of at least twice that of the highest frequency to be measured, e.g., at 300 Hz or more to measure a pulse rate of 150 beats per minute or less. In accordance with this embodiment, light of only one wavelength is needed and, thus, only one light source (e.g., a single LED) that is sensitive to blood oxygen saturation levels is needed. In an exemplary embodiment, the oximetry circuitry 244 calculates the blood oxygen saturation level and/or pulse rate in a region other than the third region 25, e.g., within another region of the auditory canal 100 or external to the auditory canal.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. An apparatus for detecting oxygen saturation levels in blood from within an auditory canal of a living being proximal to a tympanic membrane, the auditory canal being lined with tissue and including a proximal bend and a distal bend located between the proximal bend and the tympanic membrane, the apparatus comprising:

a first portion configured for placement in the auditory canal between the proximal bend and the distal bend, the first portion having a distal end extending toward the tympanic membrane when the apparatus is positioned within the auditory canal;

a second portion movably coupled to the distal end of the first portion, the second portion comprising an outer surface configured to abut at least a portion of the tissue of the auditory canal between the distal bend and the tympanic membrane when the apparatus is positioned within the auditory canal, an emitter that emits light of one or more wavelengths from a first position on the outer surface of the second portion into the tissue of the auditory canal between the distal bend and the tympanic membrane; and a detector that detects the light of one or more wavelengths from the tissue of the auditory canal between the distal bend and the tympanic membrane impinging upon a second position on the outer surface of the second portion.

2. The apparatus of claim 1, wherein the first portion is substantially rigid and the second portion extends from the first portion and is relatively flexible such that the second portion is movable relative to the first portion to at least partially isolate the second portion from movement of the first portion.

3. The apparatus of claim 1, further comprising a joint coupled between the distal end of the first portion and the second portion.

4. The apparatus of claim 1, the second portion having a proximal end coupled to the distal end of the first portion and a tympanic end extending toward the tympanic membrane when the apparatus is positioned within the auditory canal, the second portion further comprising a first hollow body portion defining an elongated passage extending between the proximal end and the tympanic end of the second portion for communication of acoustic signals through the second portion between the first portion and the tympanic membrane.

5. The apparatus of claim 4, wherein the first portion has an outer end portion substantially opposite the distal end, the first portion further comprising a second hollow body portion defining an elongated passage extending between the outer end and distal end of the first portion for communication of acoustic signals through the first portion to the first hollow body portion of the second portion.

6. The apparatus of claim 1, wherein the emitter comprises:

a light source positioned within the first portion;

an optical channel extending from the light source through the second portion to the first position.

7. The apparatus of claim 1, wherein the detector comprises:

a photo-detector positioned within the first portion;

an optical channel extending from the second position on the second portion to the photo-detector.

8. The apparatus of claim 1, further comprising:

oximetry circuitry coupled to the detector, the oximetry circuitry positioned within the first portion and configured to determine an oxygen saturation level responsive to the light detected by the detector at the second position of the second portion.

9. The apparatus of claim 1, wherein the first portion has an outer surface characterized by one or more protrusions forming one or more channels that enable the flow of air to and block light from the tissue of the auditory canal between the distal bend and the tympanic membrane when the apparatus in positioned within the auditory canal.

10. The apparatus of claim 1, wherein the first position on the outer surface of the second portion is substantially opposite the second position.

11. The apparatus of claim 1, wherein the first and second positions on the outer surface of the second portion are radial spaced relative to one another by between about 5 degrees and about 180 degrees.

12. An apparatus for detecting oxygen saturation levels in blood from within an auditory canal of a living being proximal to a tympanic membrane, the auditory canal being lined with tissue and including a proximal bend and a distal bend located between the proximal bend and the tympanic membrane, the apparatus comprising:
 a body having an outer surface configured to abut at least a portion of the tissue of the auditory canal between the distal bend and the tympanic membrane when the apparatus is positioned within the auditory canal;
 an emitter that emits light of one or more wavelengths from a first position on the outer surface into the tissue of the auditory canal between the distal bend and the tympanic membrane; and
 a detector that detects the light of one or more wavelengths from the tissue of the auditory canal between the distal bend and the tympanic membrane impinging upon a second position on the outer surface.

13. The apparatus of claim 12, wherein:
 the body includes a hollow body portion surrounded by the outer surface, the hollow body portion defining an elongated passage extending through the apparatus for communication of acoustic signals to the tympanic membrane.

14. The apparatus of claim 12, wherein the first position on the outer surface is substantially opposite the second position.

15. The apparatus of claim 12, wherein the first and second positions on the outer surface are radial spaced relative to one another by between about 5 degrees and about 180 degrees.

16. A method for detecting oxygen saturation levels in blood from within an auditory canal of a living being proximal to a tympanic membrane, the auditory canal being lined with tissue and including a proximal bend and a distal bend located between the proximal bend and the tympanic membrane, said method comprising the steps of:
 emitting one or more wavelengths of light into a first position on the tissue of the auditory canal in a first region located between the distal bend and the tympanic membrane;
 detecting the one or more wavelengths of light at a second position on the tissue of the auditory canal in the first region, the second position being spaced from the first position; and
 calculating at least one of (i) a blood oxygen saturation level and (ii) a pulse rate responsive to intensity information corresponding to the one or more wavelengths of light detected at the second position.

17. The method of claim 16, further comprising the step of:
 passing, from the first region to a second region distinct from the first region through a flexible coupling, the intensity information corresponding to the one or more wavelengths of light detected in the first region;
 wherein the step of calculating at least one of (i) the blood oxygen saturation level and (ii) the pulse rate is performed in a region other than the first region.

18. The method of claim 16, further comprising the steps of:
 blocking ambient light from external to the auditory canal from reaching the tissue surrounding the auditory canal in a region defined by the distal bend and the tympanic membrane; and
 communicating acoustic signals from external to the auditory canal to the tympanic membrane.

* * * * *